US008287933B2

(12) United States Patent  
Soulier et al.

(10) Patent No.: US 8,287,933 B2
(45) Date of Patent: Oct. 16, 2012

(54) EXTRACTS RICH IN PROANTHOCYANIDINS AND RELATING PROCESS OF PREPARATION

(75) Inventors: Chrystéle Soulier, Veyre Monton (FR); Natacha Alcouffe, St Genes Champanelle (FR); Gilles Laplaige, Guadeloupe (FR)

(73) Assignee: Ferlux S.A., Cournon d'auvergne (FR)

( * ) Notice: Subject to any disclaimer, the term of this patent is extended or adjusted under 35 U.S.C. 154(b) by 199 days.

(21) Appl. No.: 12/220,813

(22) Filed: Jul. 28, 2008

(65) Prior Publication Data

US 2009/0093537 A1    Apr. 9, 2009

(30) Foreign Application Priority Data

Aug. 1, 2007    (EP) .................................... 07113610

(51) Int. Cl.
*A23L 1/29*    (2006.01)
*B01D 15/08*    (2006.01)
*A01N 65/16*    (2009.01)

(52) U.S. Cl. ..... 426/427; 426/425; 426/489; 210/198.2; 424/732; 424/727

(58) Field of Classification Search ........................ None
See application file for complete search history.

(56) References Cited

U.S. PATENT DOCUMENTS

| 6,608,102 B1 | 8/2003 | Howell et al. |
| 2001/0021398 A1 | 9/2001 | Walker et al. |
| 2004/0156925 A1* | 8/2004 | Howell et al. ................. 424/732 |

FOREIGN PATENT DOCUMENTS

| CA | 1454896 A | 11/2003 |
| CA | 2 539 724 A1 | 4/2005 |
| CA | 1749253 | 3/2006 |
| EP | 1 388 343 A1 | 11/2004 |
| EP | 07 11 3610 | 2/2008 |
| JP | 63267774 | 11/1988 |
| WO | WO 99/12541 | 3/1999 |
| WO | WO 9912541 A1 | 3/1999 |

OTHER PUBLICATIONS

Marwan et al. Microbial Inhibitors of Cranberries; Journal of Food Science, (1986) vol. 51, No. 4 pp. 1009-1013.*
Marwan et al. Characterization of Cranberry Benzoates and Their Antimicrobial Properties; Journal of Food Science (1986) vol. 51, No. 4, pp. 1069-1070.*
Chandra et al. Isolation and Stabilization of Anthocyanins From Tart Cherries (Prunus Cerasus L.); J. Acric. Food Chem. 1993, 41, 1062-1065.*
Bourzeix et al. Suitability of water/ethanol mixtures for the extraction of catechins and proanthocyanidins from *Vitis vinifera* seeds contained in a winery by-product; Seed Sci & Tecnol. 19 (1991) 545.552.
Su et al. Identification of three flavan-3-ols from grapes; Phytochemistry 8 (1969) 1553-1558.
European Search Report dated Feb. 6, 2008; Application No. EP 07 11 3610.
Takahashi et al. "Procyanidin oligomers selectively and intensively promote proliferation of mouse hair epitheial cells in vitro and and activate hair follicle growth in vivo"; The Society for Investigative Dermatology, Inc.; (1999) 310-316.

* cited by examiner

*Primary Examiner* — Patricia Leith
(74) *Attorney, Agent, or Firm* — Abelman, Frayne & Schwab

(57) ABSTRACT

The present invention relates to extracts containing high amounts of proanthocyanidins and the relating process of preparation involving the use as starting reactants of crushed fruits, plants or already prepurified extracts rich in proanthocyanidins.

6 Claims, 2 Drawing Sheets

FIG. 2

```
Sorted By                        : Signal
Calib. Data Modified             : Thursday 18 January 2007 15:17:13
Multiplier                       : 1.0000
Dilution                         : 1.0000
Use Multiplier & Dilution Factor with ISTDs Signal 1: DAD1 E, Sig=280,16 Ref=off
Uncalibrated Peaks               : using compound Procyanidin B2
```

| Ret Time [MIN] | Type | Area [mAU*s] | Amt/Area | Amount [mg/l] | Grp | Name |
|---|---|---|---|---|---|---|
| 14.932 | VV | 1316.00208 | 3.85264e-1 | 507.00851 | | ? |
| 15.599 | VV | 102.12812 | 4.54741e-1 | 46.44182 | | ? |
| 16.182 | VV | 81.99210 | 4.73239e-1 | 38.80183 | | ? |
| 17.434 | VV | 89.01481 | 4.65837e-1 | 41.46638 | | ? |
| 17.933 | VV | 106.14445 | 4.51891e-1 | 47.96569 | | Procyanidin B2 |
| 18.828 | VV | 42.62174 | 5.59901e-1 | 23.86397 | | ? |
| 19.152 | VV | 29.81884 | 6.37393e-1 | 19.00631 | | ? |
| 19.782 | VV | 261.30582 | 4.08857e-1 | 106.83684 | | ? |
| 20.411 | VV | 253.24040 | 4.09795e-1 | 103.77667 | | ? |
| 21.018 | VV | 50.52187 | 5.31679e-1 | 26.86143 | | ? |
| 22.103 | VV | 494.07385 | 3.94988e-1 | 195.15342 | | ? |
| 22.872 | VV | 440.56726 | 3.96879e-1 | 174.85201 | | ? |
| 23.374 | VV | 206.70851 | 4.16633e-1 | 86.12159 | | ? |
| 24.305 | VV | 422.84692 | 3.97611e-1 | 168.12858 | | ? |
| 25.345 | VV | 296.36871 | 4.05375e-1 | 120.14036 | | ? |
| 26.107 | VV | 146.14180 | 4.32056e-1 | 63.14144 | | ? |
| 26.745 | VV | 130.00999 | 4.38587e-1 | 57.02073 | | ? |
| 27.295 | VV | 253.74248 | 4.09735e-1 | 103.96716 | | ? |
| 28.013 | VV | 389.70178 | 3.99158e-1 | 155.55269 | | ? |
| 28.797 | VV | 255.96692 | 4.09472e-1 | 104.81116 | | ? |
| 29.558 | VV | 523.09656 | 3.94125e-1 | 206.16519 | | ? |
| 30.160 | VV | 204.09650 | 4.17109e-1 | 85.13054 | | ? |
| 31.175 | VV | 473.07843 | 3.95679e-1 | 187.18737 | | ? |
| 32.037 | VV | 276.88333 | 4.07201e-1 | 112.74724 | | ? |
| 32.984 | VV | 503.29977 | 3.94703e-1 | 198.65391 | | ? |
| 33.492 | VV | 143.91916 | 4.32869e-1 | 62.29812 | | ? |
| 34.003 | VV | 676.52338 | 3.90789e-1 | 264.37822 | | ? |
| 35.778 | VV | 735.83820 | 3.89873e-1 | 286.88338 | | ? |
| 36.452 | VV | 321.70267 | 4.03331e-1 | 129.75254 | | ? |
| 37.093 | VV | 648.44556 | 3.91282e-1 | 253.72496 | | ? |
| 38.501 | VV | 729.89099 | 3.89958e-1 | 284.62690 | | ? |
| 39.529 | VV | 462.05762 | 3.96067e-1 | 183.00586 | | ? |
| 40.360 | VV | 851.02496 | 3.88458e-1 | 330.58741 | | ? |
| 42.215 | VV | 1060.90784 | 3.86670e-1 | 410.22094 | | ? |
| 43.035 | VV | 297.67297 | 4.05261e-1 | 120.63522 | | ? |
| 43.825 | VV | 570.42358 | 3.92904e-1 | 224.12195 | | ? |
| 44.288 | VV | 493.98444 | 3.94991e-1 | 195.11950 | | ? |
| 45.112 | VV | 623.98340 | 3.91747e-1 | 244.44356 | | ? |
| 46.211 | VV | 627.75800 | 3.91673e-1 | 245.87571 | | ? |
| 47.740 | VV | 767.23108 | 3.89445e-1 | 298.79443 | | ? |
| 48.651 | VV | 447.89734 | 3.96594e-1 | 177.63318 | | ? |
| 49.638 | MF | 325.88446 | 4.03024e-1 | 131.33919 | | ? |
| Totals : | | | | 6824.24394 | | |

Results obtained with enhanced integrator.

EXTRACTS RICH IN PROANTHOCYANIDINS AND RELATING PROCESS OF PREPARATION

FIELD OF THE INVENTION

The present invention relates to extracts containing high amounts of proanthocyanidins and the relating process of preparation involving the use as starting reactants of crushed fruits, plants or already prepurified extracts rich in proanthocyanidins.

TECHNOLOGICAL BACKGROUND

Proanthocyanidins, namely condensed tannins are ubiquitous and they are among the most abundant natural phenol derivatives. Proanthocyanidin are mixture of oligomers and polymers composed of flavan-3-ol repeating units linked through C4-C8, or C4-C6 bonds. The flavan 3-ol units may also be doubly linked to by an additional double bond between C2-O7(A-type). The dimensions of proanthocyanidins are defined by the polymerization degree (DP).

The most common flavan 3-ols-contained in proanthocyanidins are Afzalechin, Epiafzalechin, Catechin, Epicatechin, Gallocatechin, Epigallocatechin. The proanthocyanidins consisting exclusively of catechin and epicatechin are the so called procyanidins, whereas those containing afzalechin and epiafzalechin or gallocatechin and epigallocatechin are the propelargonidin and prodelphinidin. Procyanidin are the most abundant in nature.

The biological activities of proanthocyanidins that have been reported in literature include antitumour, antiinflammatory, antiageing, antioxidant, antiallergic, antibacterial especially of the urinary tract, promoting hair growth, etc (Bart Schwitters/Jack Masquelier "$21^{st}$ century Biophylaxis substance OPC, Fragrance Journal, 50-135 (1997); Tomoya Takajashi et al., Journal of investigative dermatology 112 (310.316 (1999).

Many methods are known for preparing extract enriched in proanthocyanidins from plants or fruits of various origin such as cranberry (*Vaccinium macrocarpon*), grape seeds, tea leaves, peanuts, pine bark etc.

Some of these processes encompass extraction steps carried out with aqueous alcoholic solvents in the presence of mineral acids like for example the process in CN1454896, or they encompass the use of supercritical solvents like $CO_2$ as disclosed in CN174923, or they require the use of ultra filtration membrane or involve reverse osmosis filtration as in the process disclosed in JP63267774.

Other processes require a combination of multiple extractions steps, using several type of organic solvents either alone or combined with each other, associated by at least one step wherein a solution containing the extracts is absorbed on a macroreticular polymeric resin, the absorbed liquid is subsequently eluted, concentrated and atomised as disclosed in the processes described in U.S. Pat. No. 6,608,102, U.S. Pat. No. 6,440,471.

According to other processes it is possible to obtain extracts containing very high amounts of proanthocyanidins. For example it is possible to obtain extracts with total proanthocyanidins content ranging from 80-90% with oligomer proanthocyanidins (OPC) in amounts of from 23 to 45% with the process disclosed in CA2539724 involving the treatment of a plant like pine bark or an extract or juice thereof, with at least two type of a absorbents resins differing in at least one of the following characteristics, namely the type of material, pore radius, specific surface area and molecular weight distribution range or it is possible to obtain extracts having a total proanthocyanidins content of from 67 to 85% and an OPC content of from 12.5 to 51%, with the process disclosed in EP1602653 comprising subjecting an extract or a squeezed juice of a plant to a combination of a treatment with a salt or an alkaloid and a treatment with a synthetic absorbent. resin Notwithstanding the plethora of prior art processes allowing to obtain extract having a high titre in proanthocyanidins, commercially available extracts have a proanthocyanidins titre not exceeding 7%.

This means therefore that the prior art processes for preparing extract having a high titre in proanthocyanidins are not easily realisable on an industrial scale, for many reasons such as for example the use of toxic extraction solvents or extreme extraction temperature (about 100° C.) for long period of times (about 24 hours), the use of under pressure devices like in the case of supercritical fluids, or the use of ultrafiltration membrane.

The need was therefore felt to have a process for preparing extracts having a high proanthocyanidins titre not suffering the drawback of the prior art processes and that therefore could be easily realisable on an industrial scale.

SUMMARY OF THE INVENTION

The Applicant has found a process easily realisable on an industrial scale allowing to obtain an extract having a high titre in proanthocyanidins.

This process allows to obtain an extract rich in proanthocyanidins starting from already prepurified extracts or from fruits or plants rich in proanthocyanidins, and comprises the following steps:

a) extracting at room temperature a crushed fruit or plants containing high amounts in proanthocyanidins or an already prepurified extract rich in proanthocyanidins with aqueous ethanol, having an ethanol concentration ranging from 50 to 80% by volume,
b) filtering the mixture coming from step (a),
c) concentrating the filtered solution coming from step (b) under vacuum,
d) optionally storing the concentrated product coming from step (c) which products was optionally previously diluted with demineralized water, for a time ranging from 5 to 24 hours,
e) diluting with demineralised water the concentrated stored product coming from step (c) or that coming from (d) in case this dilution with water was not carried out in step (d),
f) filtering the mixture coming from step (e)
g) loading the solution on a macroreticular aliphatic crosslinked polymeric resin,
h) washing with water said resin,
i) eluting the polymeric macroreticular aliphatic crosslinked resin coming from step (h) with aqueous ethanol having an ethanol content of from 50 to 80% by volume,
j) concentrating the eluted solution coming from the previous step under vacuum,
k) drying the concentrated product coming from step (j) under vacuum, or by spray drying.

This process allows to obtain extracts containing more than 10% proanthocyanidins, preferably more than 15%, even more preferably more than 20%, by using mild extraction conditions with aqueous ethanol, and also only one absorption with a macroreticular polymeric resin using in the desorption step non toxic solvents like aqueous ethanol.

DESCRIPTION OF THE FIGURES

FIG. 2: the retention times the area the corresponding concentration expressed in mg/ml of each peak, and finally the total concentration of the analysed sample as prepared as described in Example 1.

DETAILED DESCRIPTION OF THE INVENTION

Figure 1:
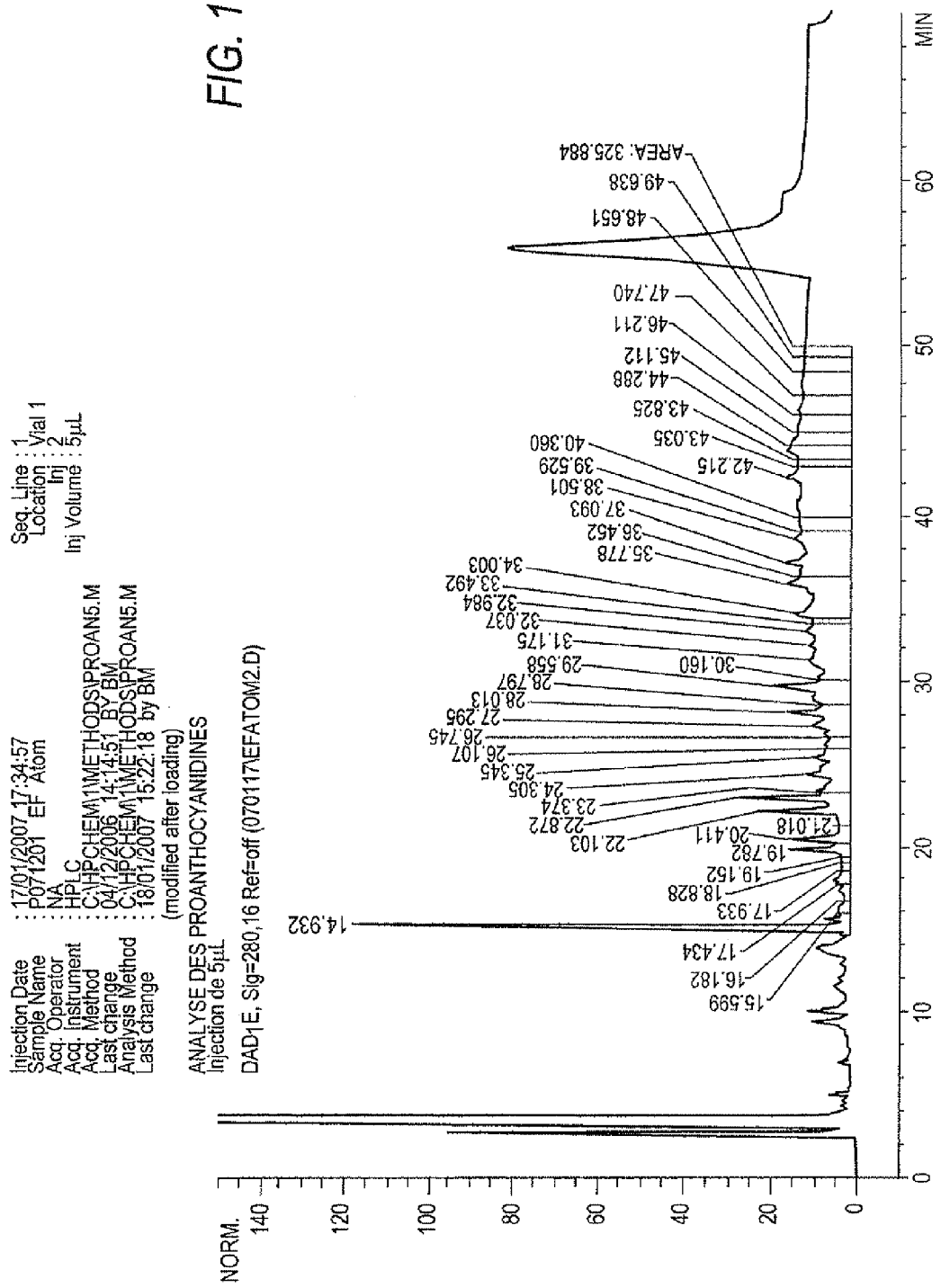
FIG. 1 reports the HPLC chromatogram.

As fruit or plants rich in proanthocyanidins for the purpose of the present invention we mean for example cranberry, apple, blackberry, grapes, plum, pomegranate, raspberry, strawberry, broad bean, lentil, tea.

Preferably in the process according to the present invention cranberry (*Vaccinium macrocarpon*) is used as the starting material In step (a) the extraction solvent has preferably an ethanolic content of from 60 to 75%, more preferably 70% by volume.

The extraction time is preferably comprised between 10' to 2 hours, more preferably is 30'.

The process according to the present invention, when as the starting material in step (a) a crushed fruit or plant is used, encompasses a further step, wherein said crushed fruit or plant coming from the extraction step (a) with aqueous ethanol is pressed before the filtration of step (b) is carried out.

Step (d) is an optional step and in any case, when this step is carried out, the storing time is preferably comprised between 8 h and 20 hours, more preferably 15 hours.

The washing with demineralized water of the resin containing the absorbed solution, namely step (h) of the process of the invention is conducted with the purpose of removing sugars and phenolic acid.

In case the fruit is also rich in anthocyanins the process may comprise a further washing step, after the washing step with water, to remove anthocyanins from the resin with aqueous methanol having a methanol content of 60% (volume/volume)

In step (i) the concentration of the eluting solvent, namely aqueous ethanol has an ethanol content of from 60 to 75% by volume more preferably 70% by volume. The macroreticular aliphatic crosslinked resin utilised in said step may be selected from those already known and commercially available.

Step (j) is preferably carried out under vacuum at temperatures comprised between 35 and 45° C., more preferably at 40° C.

The applicant has also optimised an analytical method to determine by HPLC the titre of proanthocyanidins in the final extract.

This method comprises two separate steps:
1. The purification of the extract to be analysed
2. the analysis.

Step 1: Purification of the Extract to be Analysed
Preparation of Sephadex LH20 Column 10 g of Sephadex LH20 were swelled with demineralised water (about 50 ml) in at least 3 hours, and then introduced into a glass column C16 sold by Pharmacia Biotech. The resin was washed with about 130 ml of demineralised water.
Preparation of the Solution to be Loaded onto the SEPHADEX LH20 Resin.

With the purpose of obtaining a tenor of compounds absorbing at λ=280 nm loaded onto the column was always approximately the same, a spectrophotometric analysis was carried out.

The extracts or the solution was diluted in 20% methanol to obtain an absorbance ranging from 32 to 48 (or after dilution at 1/50 ABS=0.8±20%) at λ=280 nm.

Purification on Sephadex LH20

The solution diluted with methanol 20% with the absorbance comprised in the aforementioned range was centrifuged for 15 minutes at 4000 rpm.

20 ml of this decanted solution was charged onto the aforesaid resin and the following three elutions were carried out:
Elution 1, 80 ml methanol 20%,
Elution 2, 160 ml methanol 60%,
Elution 3, 240 ml methanol 100%.

These elutions were conducted at a flow rate of about 2 ml/min. The eluted solution coming from elution 1 and 2 were discarded.

The first 20-30 ml of the solution coming from elution 3 were discarded then the remaining eluted solution was collected.

The solvent was removed by evaporation from the eluted solution and the obtained residue was dried.

The dry extract was diluted in a mixture of acetone/water/acetic acid having the following volumetric ratio 79:29.5:0.5 for being analysed by HPLC, in order to obtain a final volume comprised between 1 and 1.7 ml, this volume was indicated as $V_1$.

2. The HPLC Analysis
Calibration Table

The standard utilised for the analysis of proanthocyanidins is Procyanidin B2 (Epicatechin 4β→8)

The following solutions were prepared as reported in the following table

| Solution | procyanidin B2 (mg) | Acetone/water/acetic acid (70:29.5:0.5) (ml) |
|---|---|---|
| 1 | 0.15 | 10 |
| 2 | 0.75 | 5 |
| 3 | 1.7 | 5 |
| 4 | 0.6 | 1 |
| 5 | 0.9 | 1 |

Calculation of the Concentration of Procyanidin B2

$$C_{B2}=(m\times 1000)/V$$

wherein $C_{B2}$ is the concentration of procyanidin B2 in mg/l
m is the weight of procyanidin in mg
V is the volume of acetone/water/acetic acid in ml.
HPLC Conditions:
Column:
Luna silica 5 μm (250×4.6 mm) Phenomenex,
Detecting cartridge (? Cartouche de garde) 3 mm
Elution Solvents:
Solvent (A): Methanol,
Solvent (B): Dichloromethane,
Solvent (C): Acetic acid/water (1:1) (V/V)

| Elution times (min) | Solvent (A) (%)[1] | Solvent (B) (%)[1] | Solvent (C) (%)[1] |
|---|---|---|---|
| 0 | 14.0 | 82.0 | 4 |
| 20 | 23.6 | 72.4 | 4 |
| 50 | 35.0 | 61.0 | 4 |
| 55 | 86.0 | 10.0 | 4 |
| 65 | 86.0 | 10.0 | 4 |
| 70 | 14.0 | 82.0 | 4 |

[1]Volume percentages
Elution flow-rate: 1 ml/min
Column temperature: 37° C.
Spectra range: 200-700 nm
Wave length: $\lambda = 280$ nm
Injected volume = 5 µl Standard Solution Analyses The aforementioned standard solutions were analysed by HPLC After the analysis the calibration table is inserted in HPLC software (area as a function of procyanidin B2 concentration).

Analysis of the Sample

The diluted sample in acetone/water/acetic acid (70:29:0.5) was analysed by HPLC.

Chromatogram Analysis

Cranberries *vaccinium macrocarpon* obtained after purification and HPLC analysis were identified by mass spectrometry the proanthocyanidins are the peaks having retention time of from 13.5 and 50 minutes.

The integration method was derived from "Fractionation of polymeric from low bush blueberry and quantification of procyanidins in selected foods with optimised normal phase HPLC.MS fluorescent detection method", Gu L. Kelm et al J. Agr, Food Chem. 2002, 50, 4852-4860)

It consists in drawing a flat base line from the beginning of the run until the end. A perpendicular line was drawn from the lowest point of the valley between adjacent peaks of oligomers to the flat base line. The area enclosed by the curve peaks two adjacent perpendicular lines and the flat base line was integrated. This area must be comprised in the above calibration table.

Analysis of the Obtained Data

The HPLC software allows to calculate the proanthocyanidins concentration (mg/l) of the analysed solution.

The calibration table of procyanidin B2 allows to have the proanthocyanidins concentration corresponding to the area of each peak.

The concentration of each peak of proanthocyanidins was added, the results correspond to the concentration of proanthocyanidins of the analysed solution ($C_{LUE}$ in mg/l).

Namely the concentration in proanthocyanidins C (mg/l) of the solution charged on Sephadex, expressed in equivalent of procyanidin B2 may be obtained applying the following equation:

$$C=(C_{LUE} \times V_1)/20$$

Wherein $V_1$: volume of the analysed solution (1-1.7 ml)

We report herein below for illustrative but not limitative purposes the examples of preparation starting from crushed cranberry (example 1) and starting from already prepurified extracts (example 2).

Example 1

Extract Rich in Proanthocyanidins from Crushed Cranberry 50 kg of crushed cranberry (*Vaccinium macrocarpon*), 100 l of aqueous ethanol 70% (V/V) were stirred for 30 minutes, afterwards the crushed fruits were pressed and the whole mixture was filtered on a 25 µm sieve thereby obtaining a clear ethanolic extract weighing about 120 kg.

This ethanolic extract was concentrated under vacuum at a temperature of 40° C. thereby obtaining a residue weighing about 10 kg. It was then diluted with 10 l of demineralised water thereby obtaining a diluted extract weighing about 20 kg, which is stored at room temperature for 15 hours.

The diluted extract was then filtered on a 10 µm sieve 25 l of a commercial macroreticular aliphatic crosslinked resin were washed with 75 l of demineralized water, then they were charged onto a glass column and added with 20 kg of the aforesaid filtered aqueous solution. The resin with the adsorbed extracts was washed with 100 l of demineralized water and then it was eluted with 100 l of ethanol 70% V/V.

The eluted solution was then concentrated under vacuum at 40° C. thereby obtaining about 20 kg of concentrated extract, which is finally atomized thereby obtaining a powder.

The extract was analysed with the analytical method above reported, FIGS. 1 and 2 report the HPLC chromatogram, the retention times the area of each peak and the corresponding concentration expressed in mg/ml of each peak, and finally the total concentration of proanthocyanidins or $C_{LUE}$ which is 6824.24 mg/l V1=1.7 ml (total analysed solution by HPLC).

Therefore if we apply the above equation $$C=(C_{LUE} \times V1)/20$$

$$C=6824.24 \times 1.7/20=580.06 \text{ mg/l}$$

An aqueous methanolic (MeOH 20%) solution was prepared with 201.5 mg of the final extract, whose volume=$V_2$=72 ml.

580.06×0.072=41.76 mg of proanthocyanidins (41.76/201.5)×100=20.73%.

Example 2

Extracts Prepared from Already Prepurified Extracts

The cranberry extract used for this trial is EXOCYAN CRAN 10, produced by Tournay technologies batch No L7015, which was analysed with the above disclosed method.
Content in proanthocyanidins: 7%

607.7 mg of the cranberry extract were treated with 100 ml 70% (V/V) for 30 minutes. The solution was filtered and then concentrated under vacuum by using the modalities of Example 1, and stored for 1 night.

The concentrated solution was diluted with 10 ml of demineralised water then filtered.

The solution was loaded on a commercial macroreticular aliphatic crosslinked resin, then rinsed with water (200 ml) and eluted with 70% ethanol the solution obtained was concentrated under vacuum.

The concentrated obtained was dried and the final extract obtained (158.2 mg) was analysed. Its proanthocyanidin content evaluated with the above method is 18.0%.

Therefore the concentration of proanthocyanidins in the final extract was 2.6 times higher than in the starting extract.

The invention claimed is:

1. A process for obtaining an extract having a proanthocyanidins titre higher than 10% obtained from cranberry or already prepurified extracts of cranberry comprising:

(a) contacting a proanthocyanidin containing crushed cranberry fruit or an already prepurified extract of cranberry with an aqueous ethanol solvent, at an ethanol concentration ranging from 60 to 75% by volume, for a time ranging from 10 minutes to 2 hours, (b) filtering the mixture coming from step (a), (c) concentrating the filtered solution coming from step (b) under vacuum, to obtain a concentrate, (d) storing said concentrate at room temperature for a time ranging from 5 to 24 hours, (e) diluting the stored concentrate with demineralized water to obtain a mixture, (f) filtering the mixture coming from step (e), to obtain a solution, (g) loading the solution of step (f) on a macroreticular aliphatic crosslinked polymeric resin, (h) washing said resin with demineralized water, (i) eluting the polymeric macroreticular aliphatic crosslinked resin of step (h) with aqueous ethanol having an ethanol content of from 50 to 80% by volume, to obtain an eluted solution having a proanthocyanidin titre higher than 10%, (j) concentrating the eluted solution coming from the previous step (i) under vacuum, to obtain a concentrated product, and (k) drying the concentrated product coming from step (j) under vacuum, or spray drying, to obtain said extract.

2. The process according to claim 1, wherein said aqueous ethanol has an ethanol solvent of step (a) content of 70% by volume.

3. The process according to claim 1, wherein the time of step (a) is 30 minutes.

4. The process according to claim 1, wherein the crushed cranberry fruit is pressed before carrying out step (b).

5. The process according to claim 1, comprising storing said concentrate product for from 8-20 hours.

6. The process according to claim 1, wherein said storage time is 15 hours.

* * * * *